(12) United States Patent
Strickland, Jr.

(10) Patent No.: US 6,761,165 B2
(45) Date of Patent: Jul. 13, 2004

(54) MEDICAL VENTILATOR SYSTEM

(75) Inventor: James H. Strickland, Jr., Birmingham, AL (US)

(73) Assignee: The UAB Research Foundation, Birmingham, AL (US)

(*) Notice: Subject to any disclaimer, the term of this patent is extended or adjusted under 35 U.S.C. 154(b) by 380 days.

(21) Appl. No.: 09/791,368

(22) Filed: Feb. 23, 2001

(65) Prior Publication Data

US 2001/0039951 A1 Nov. 15, 2001

Related U.S. Application Data

(60) Provisional application No. 60/185,669, filed on Feb. 29, 2000.

(51) Int. Cl.$^7$ .............................................. A61M 16/00
(52) U.S. Cl. ........................ 128/204.22; 128/204.18; 128/204.21; 128/204.23; 128/205.11
(58) Field of Search ..................... 128/204.18, 204.23, 128/205.11, 204.21, 204.22

(56) References Cited

U.S. PATENT DOCUMENTS

| | | | |
|---|---|---|---|
| 4,163,450 A | 8/1979 | Kirk et al. | 128/145.8 |
| 4,182,599 A | 1/1980 | Eyrick et al. | 417/328 |
| 4,281,651 A | 8/1981 | Cox | 128/204.23 |
| 4,326,513 A * | 4/1982 | Schulz et al. | 128/203.14 |
| 4,584,996 A | 4/1986 | Blum | 128/204.21 |
| 4,612,928 A | 9/1986 | Tiep et al. | 128/204.23 |
| 4,776,333 A | 10/1988 | Miyamae | 128/204.21 |
| 4,827,935 A | 5/1989 | Geddes et al. | 128/419 G |
| 4,838,257 A | 6/1989 | Hatch | 128/204.18 |
| 4,889,116 A | 12/1989 | Taube | 128/204.23 |
| 5,003,985 A | 4/1991 | White et al. | 128/716 |
| 5,103,814 A | 4/1992 | Maher | 128/204.18 |
| 5,190,038 A | 3/1993 | Polson et al. | 128/633 |
| 5,365,922 A | 11/1994 | Raemer | 128/204.23 |
| 5,388,575 A | 2/1995 | Taube | 128/204.23 |
| 5,398,680 A | 3/1995 | Polson et al. | 128/633 |
| 5,448,991 A | 9/1995 | Polson et al. | 128/633 |

OTHER PUBLICATIONS

Noll et al. "Weaning from Mechanical Ventilation—Usefulness of measures of Svo2, Spo2, vital signs, and derived dual oximetry parameters as indicators of arterial blood gas variables during weaning of cardiac surgery patients from mechanical ventilation" Heart & Lung, vol. 24, No. 3, p. 220–226, Jun. 1995.

Abstract of Dojat et al. "A knowledge–based system for assisted ventilation of patients in intensive care units" Int. J. Clin. Monit. Comput., vol. 9, No. 4, p. 239–50, Dec. 1992.

510(k) Servo Ventilator 300A brochure, Siemans–Elema AB.

Strickland, Jr. et al. "A Computer–controlled Ventilator Weaning System" Chest, vol. 100, p. 1096–1099, Oct. 1991.

Strickland, Jr. et al. "A Computer–controlled Ventilator Weaning System, A Clinical Trial" Chest, vol. 103, p. 1220–1226, Apr. 1993.

Linton et al. "Automatic Weaning From Mechanical Ventilation Using an Adaptive Lung Ventilation Controller" Chest, vol. 106, p. 1843–1850, Dec. 1994.

* cited by examiner

Primary Examiner—Glenn K. Dawson
Assistant Examiner—Darwin P Erezo
(74) Attorney, Agent, or Firm—Gifford, Krass, Groh, Sprinkle, Anderson & Citkowski, P.C.

(57) ABSTRACT

A medical ventilator system is disclosed which automatically controls and modifies the oxygen support provided to the patient. The system includes a source of pressurized oxygen and a fluid conduit extending between the pressurized oxygen source and a patient. A valve is fluidly connected in series with the conduit which is variably controllable to vary the oxygen support for the patient. A pulse oximeter provides an $SpO_2$ signal representative of the blood saturation of the patient. A controller is responsive to the magnitude of the $SpO_2$ signal as well as the rate of change of the $SpO_2$ signal for varying the oxygen support ($FiO_2$) to the patient by variably actuating the valve. Preferably, the controller utilizes fuzzy logic to determine the proper oxygen support for the patient.

5 Claims, 4 Drawing Sheets

MEDICAL VENTILATOR SYSTEM

RELATED APPLICATION

This application claims priority of U.S. Provisional Patent Application No. 60/185,669 filed Feb. 29, 2000, which is incorporated herein by reference.

BACKGROUND OF THE INVENTION

I. Field of the Invention

The present invention relates generally to medical ventilators.

II. Description of the Prior Art

Medical ventilator systems have been long used to provide supplemental oxygen support to patients unable to breathe normally on their own accord. These previously known medical ventilators typically comprise a source of pressurized oxygen which is fluidly connected to the patient through a fluid conduit.

A variably actuatable valve is connected in series with the fluid conduit to vary the fraction of positive pressure inspired oxygen ($FiO_2$) to the patient. $FiO_2$ will vary between 0.21, in which no supplemental oxygen support is provided to the patient, and 1.0, in which pure oxygen is provided to the patient.

In order to determine the proper $FiO_2$, the arterial oxygen saturation ($SpO_2$) is typically monitored via a pulse oximeter attached to the patient. The $SpO_2$ is ideally in the range of 0.97–1.0 whereas an $SpO_2$ of less than 0.91 is dangerously low. Consequently, the $FiO_2$ should be increased as the $SpO_2$ decreases.

Many of these previously known medical ventilators are manually controlled, i.e. the patient is continuously monitored by medical personnel and the $FiO_2$ adjusted accordingly. Such systems, however, are disadvantageous not only since they require extensive medical attention by medical personnel, but are inherently inaccurate. Such inaccuracies increase the amount of time necessary to wean the patient from the ventilator system.

There have, however, been attempts to automate the adjustment of $FiO_2$ as a function of the patient's $SpO_2$. Many of these previously known systems, however, merely adjust the amount of $FiO_2$ in preset increments as a function of the value of the $SpO_2$. For example, if the $SpO_2$ falls below a preset threshold, the $FiO_2$ is increased in preset increments until the $SpO_2$ is above the threshold level. Conversely, if the $SpO_2$ increases past a maximum threshold, e.g. 0.99, the $FiO_2$ is decreased in preset increments until the $SpO_2$ is between the upper and lower thresholds.

While these previously known automated ventilation systems have effectively reduced the amount of required medical attention for the patient, they have not significantly reduced the amount of time necessary to wean the patient from the medical ventilator.

SUMMARY OF THE PRESENT INVENTION

The present invention provides a medical ventilator system which overcomes all of the above-mentioned disadvantages of the previously known devices.

In brief, the medical ventilator system of the present invention comprises a source of pressurized oxygen which is fluidly connected to the patient via a fluid conduit or breathing tube. A variably actuatable valve is fluidly connected in series with the conduit so that the $FiO_2$ support for the patient varies as a function of the valve actuation.

The ventilator system further includes a controller for controlling the actuation of the valve and thus the $FiO_2$ support to the patient. The controller is preferably microprocessor based and receives an $SpO_2$ signal from a pulse oximeter attached to the patient. The controller then outputs control signals to the valve to control the valve actuation and thus the $FiO_2$ support to the patient.

In one embodiment of the invention, the controller monitors not only the magnitude of the $SpO_2$ signal, but also the rate of change of the $SpO_2$ signal. The controller then utilizes the magnitude and rate of change of the $SpO_2$ signal to calculate a $\Delta FiO_2$ value, i.e. the amount of change of the $FiO_2$ support to the patient, in accordance with a preset formula.

In a second embodiment of the invention, however, the controller utilizes fuzzy logic in lieu of the preset formula in order to calculate the $\Delta FiO_2$. The fuzzy logic effectively utilizes a lookup table to increase the $\Delta FiO_2$ by a greater amount as the patient's $SpO_2$ becomes lower.

In practice, the medical ventilator of the present invention not only safely and effectively provides ventilation support for the patient, but also effectively reduces the amount of time required to wean the patient from the ventilator.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF PREFERRED EMBODIMENTS OF THE PRESENT INVENTION

Figure 1:
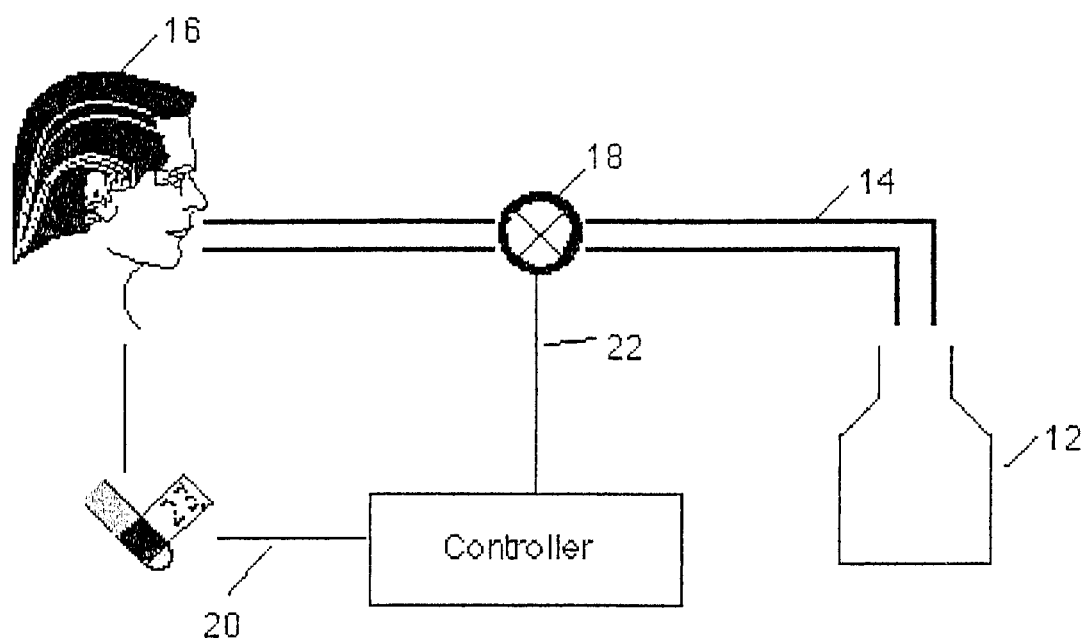
FIG. 1 is a diagrammatic view illustrating the ventilation system of the present invention.

With reference first to FIG. 1, a diagrammatic view of a preferred embodiment of the invention is there diagrammatically illustrated. The ventilator system 10 includes a source 12 of pressurized oxygen which is fluidly connected by a fluid conduit 14 to a patient 16. A valve 18 is fluidly connected in series with the fluid conduit 14. This valve 18 is variably actuatable to thereby vary the fraction of positive pressure inspired oxygen ($FiO_2$) support for the patient.

A microprocessor based controller 20 controls the actuation of the valve 18 through a control line 22. Any appropriate interface, such as an RS-232 interface, is provided between the processor 20 and the valve 18. Furthermore, the controller 20 receives a signal representative of the arterial oxygen saturation ($SpO_2$) from a pulse oximeter 23 attached to the patient 16 through an input line 24.

Figure 2:
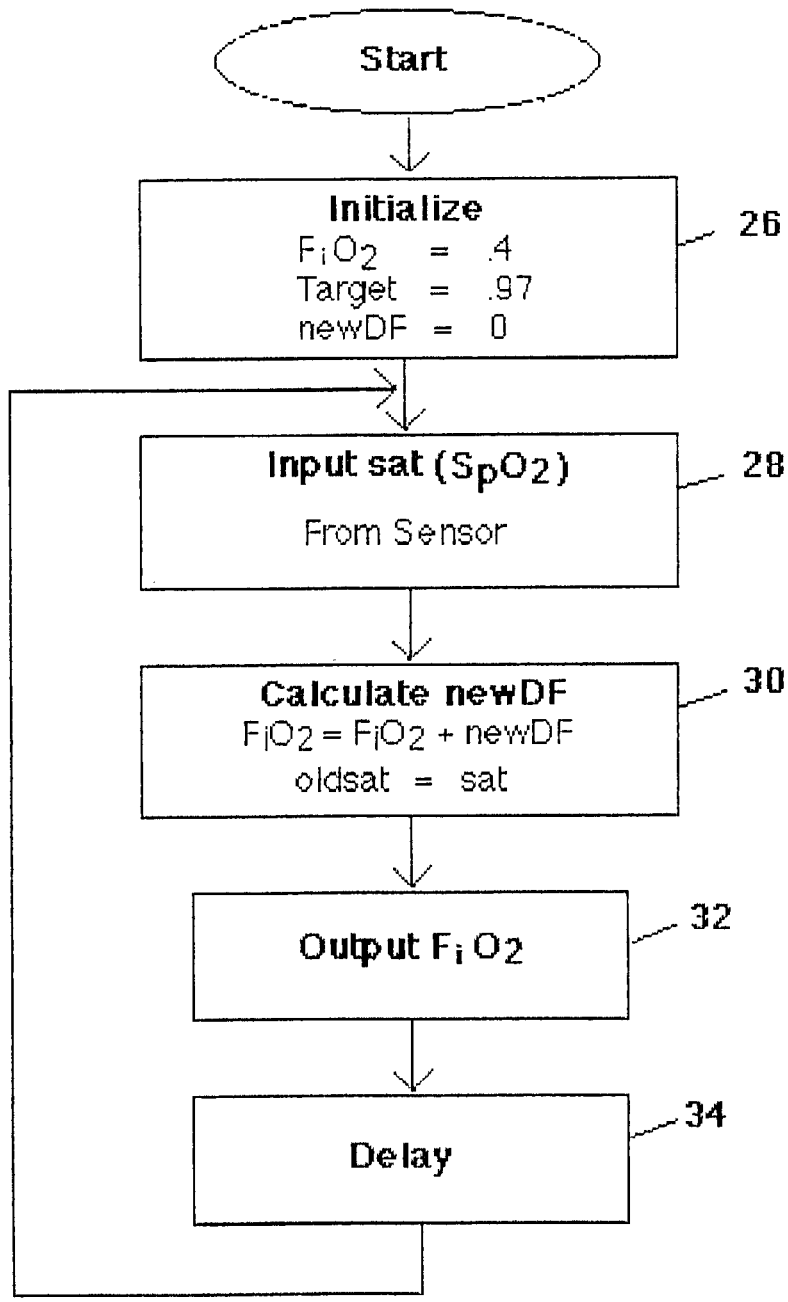
FIG. 2 is a flow chart illustrating the operation of a preferred embodiment of the present invention.

With reference now to FIG. 2, the main loop of a program executed by the controller 20 to control the $FiO_2$ support to the patient is there shown. At step 26, the program initializes several variables, such as the initial $FiO_2$, the target $SpO_2$ (Target), as well as the differential $FiO_2$, i.e. the amount of change for the $FiO_2$ support. Step 26 then branches to step 28.

At step 28, the program inputs the oxygen saturation signal $SpO_2$ from the oximeter 23 and stores this as variable "sat." Step 28 then branches to step which calculates the desired change "newDF" of the $FiO_2$ support in a fashion subsequently described in greater detail. Step 30 then adds the variable newDF to the current value for $FiO_2$ so that the new value of $FiO_2$ represents the newly calculated desired $FiO_2$ support to the patient. Step 30 also saves or stores the value of sat in a variable "oldsat" and then branches to step 32.

At step 32, the controller 20 outputs the appropriate signal on output line 22 to the valve 18 in order to provide the newly calculated value $FiO_2$ support to the patient. Step 32 then branches to step 34 which introduces a predetermined delay, e.g. two seconds, and then branches back to step 28 where the above process is repeated.

Figure 3:
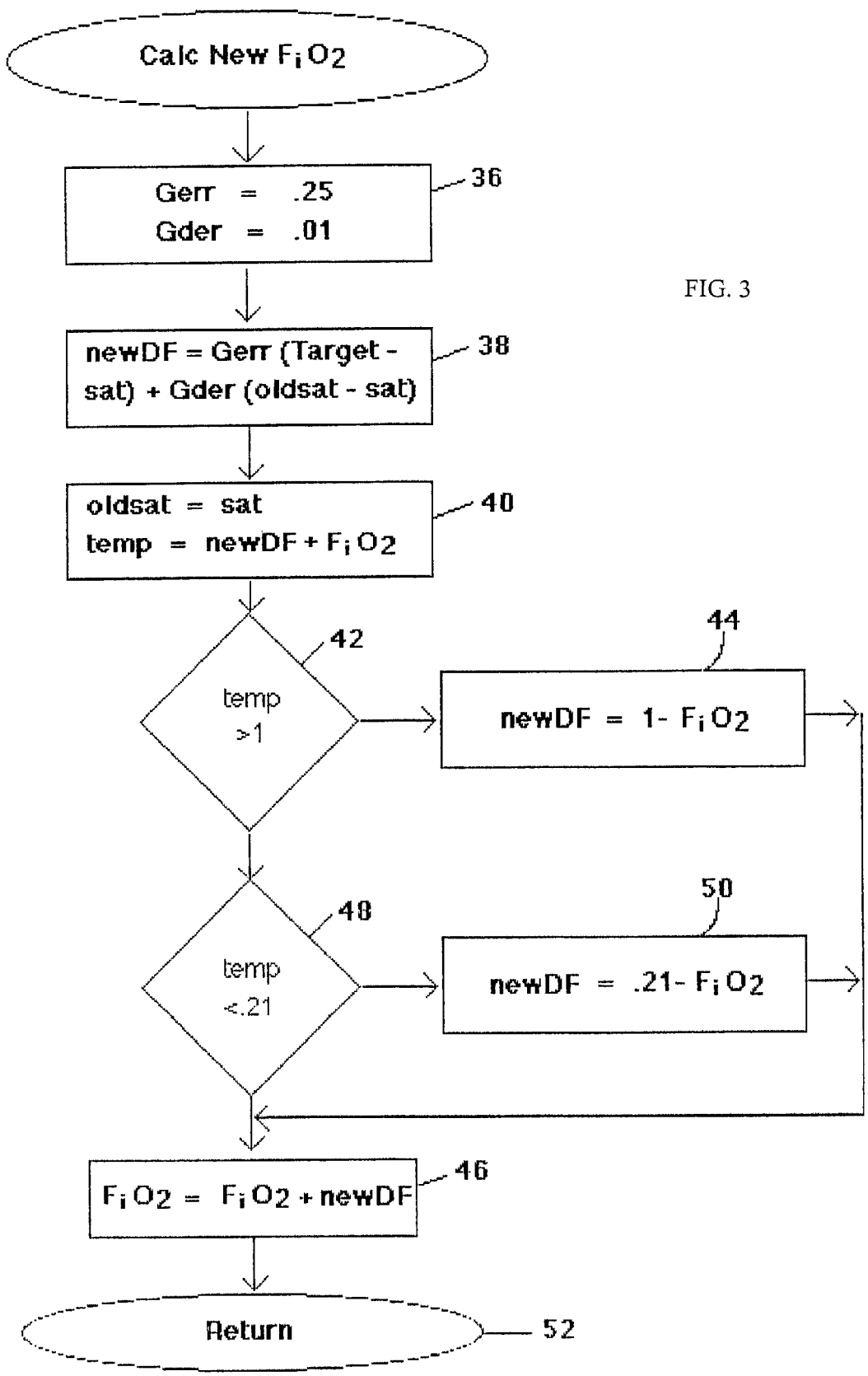
FIG. 3 is a flow chart illustrating a portion of one preferred embodiment of the present invention.

With reference now to FIG. 3, a first preferred embodiment for calculating the new value of $FiO_2$, i.e. step 30 in FIG. 2, is illustrated. At step 36 two constants, Gerr and Gder, are set to predetermined values. The constant Gerr is utilized to calculate the variable newDF as a function of the magnitude of the oxygen saturation sat as determined at step 28 (FIG. 1), while the constant Gder is used to vary the incremental change newDF of the $FiO_2$ support as a function of the rate of change of the patient's $SpO_2$.

Specifically, step 36 branches to step 38 where the variable newDF is calculated in accordance with the following formula:

$$newDF = Gerr(Target - sat) + Gder(oldsat - sat).$$

Step 38 then branches to step 40 in which the patient's current oxygen saturation sat is stored as variable oldsat. Additionally, step 40 calculates a temporary variable temp for the new value of $FiO_2$ in accordance with the following formula:

$$temp = FiO_2 + newDF.$$

Step 40 then branches to step 42.

The amount of pressurized oxygen support $FiO_2$ cannot exceed 1.0, i.e. 100%. Consequently, at step 42, the variable temp is compared with 1 and, if temp is greater than 1, step 42 branches to step 44 in which newDF is calculated in accordance with the following formula:

$$newDF = 1 - FiO_2$$

and step 44 then branches to step 46.

Assuming that temp is not greater than the value 1, step 42 instead branches to step 48 in which the temporary calculated value for $FiO_2$ temp is compared with the value 0.21 representative of the normal oxygen content of the atmosphere. Since oxygen support less than the normal oxygen content of the atmosphere is never required, if temp is less than 0.21, step 48 branches to step 50 in which the value newDF is calculated in accordance with the following formula:

$$newDF = 0.21 - FiO_2.$$

Step 50 then branches to step 46.

At step 46, the new value for $FiO_2$ is calculated in accordance with the following formula:

$$FiO_2 = FiO_2 + newDF.$$

Step 46 then branches to step 52 in which control of the subroutine illustrated in FIG. 3 returns to step 32 in the main program loop (FIG. 2).

From the foregoing, it can be seen that the variable $FiO_2$, i.e. the pressurized oxygen support for the patient, is incremented or decremented in an amount equal to newDF as determined by the subroutine illustrated in FIG. 3. Consequently, the calculation of the incremental change newDF in the $FiO_2$ variable is varied not only as a function of the magnitude of the $SpO_2$ signal from the pulse oximeter 22, but also as a function of the rate of change of the patient's $SpO_2$. Furthermore, since the controller 20 is microprocessor based, the impact on the $FiO_2$ of both the magnitude of the $SpO_2$ as well as the rate of change of the $SpO_2$ can be easily modified by changing the variables Gerr and Gder.

In the second preferred embodiment of the invention, the ventilator system utilizes fuzzy logic to calculate newDF, i.e. the incremental change in $FiO_2$ support, and thus the $FiO_2$ oxygen support to the patient. The fuzzy logic calculation of the newDF thus replaces the subroutine illustrated in FIG. 3 as well as step 30 in FIG. 2 of the drawing.

Figure 4:
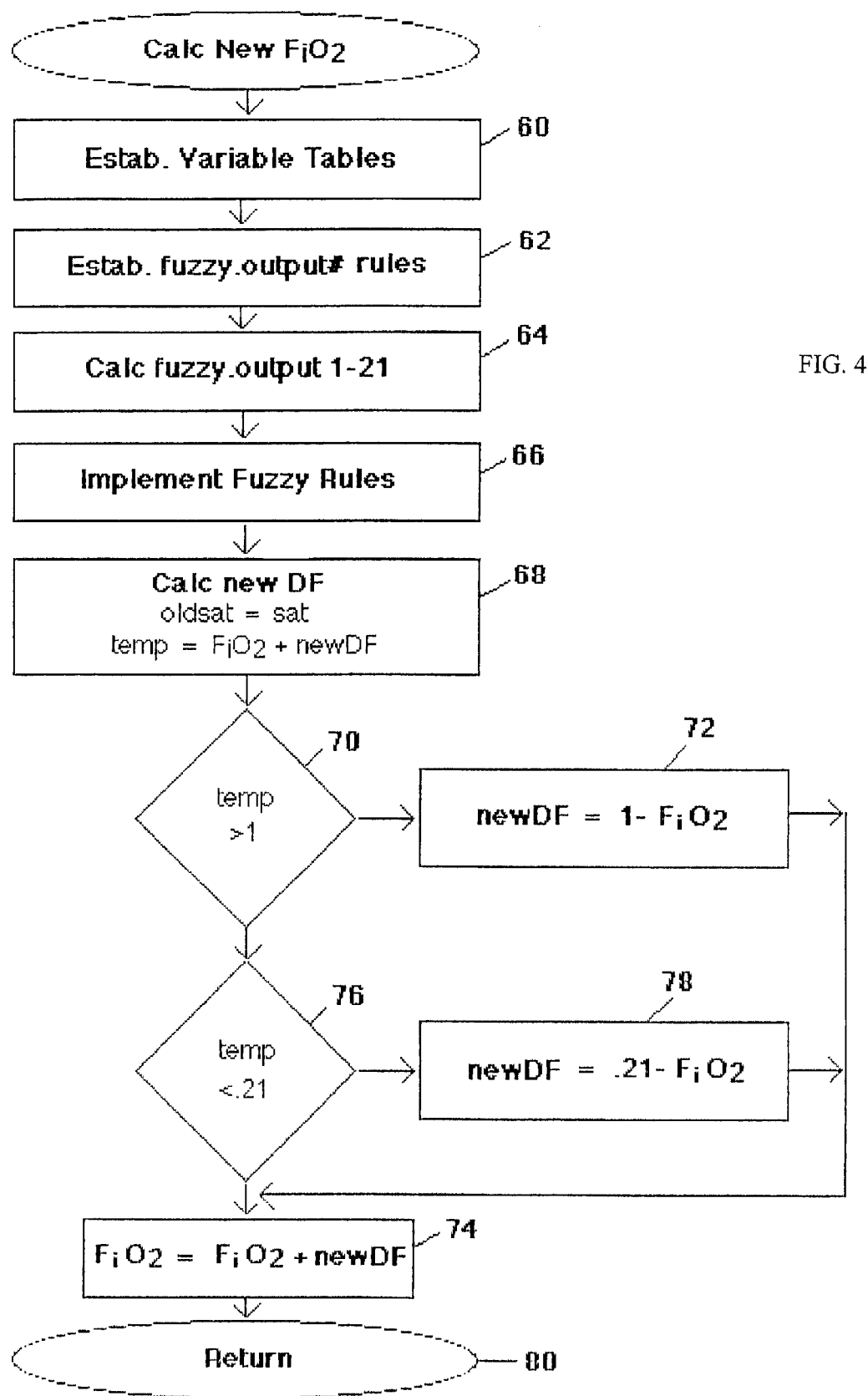
FIG. 4 is a flow chart similar to FIG. 3 but illustrating a second preferred embodiment of the present invention.

With reference to FIG. 4, in implementing the fuzzy logic determination of the newDF, the program initially establishes the following table at step 60 in which variables fuzzy.vln-fuzzy.lp are established as a function of the oxygen saturation "sat" determined at step 28 (FIG. 2) in accordance with the following Table 1:

TABLE 1

| sat | fuzzy.vln | fuzzy.ln | fuzzy.mn | fuzzy.sn | fuzzy.normal | fuzzy.sp | fuzzy.lp |
|---|---|---|---|---|---|---|---|
| <.91 | 1 | | | | | | |
| .91 | 1 | | | | | | |
| .92 | .333 | .6667 | | | | | |
| .93 | | .667 | .3333 | | | | |
| .94 | | | 1 | | | | |
| .95 | | | .333 | .6667 | | | |
| .96 | | | | .6667 | .3333 | | |
| .97 | | | | | 1 | | |
| .98 | | | | | .3333 | .6667 | |
| .99 | | | | | | .6667 | .3333 |
| 1 | | | | | | | 1 |

Additionally, the program establishes three variables fuzzy.dsn, fuzzy.dszero and fuzzy.dsp as a function of whether the patient's oxygen saturation stored in sequential variables oldsat and sat is increasing, constant or decreasing in accordance with the following Table 2:

TABLE 2

| | fuzzy.dsn | fuzzy.dszero | fuzzy.dsp |
|---|---|---|---|
| oldsat > sat | 1 | | |
| oldsat = sat | | 1 | |
| oldsat < sat | | | 1 |

At step 62, the program establishes the variables fuzzy.output1-fuzzy.output21 as a function of both fuzzy.vln-fuzzy.1p variables as well as a function of fuzzy.dsn-fuzzy.dsp variables:

TABLE 3

| output | fuzzy.vln | fuzzy.ln | fuzzy.mn | fuzzy.sn | fuzzy.normal | fuzzy.sp | fuzzy.lp | fuzzy.dsn | fuzzy.zero | fuzzy.dsp |
|---|---|---|---|---|---|---|---|---|---|---|
| fuzzy.output1 | X | | | | | | | X | | |
| fuzzy.output2 | X | | | | | | | | X | |
| fuzzy.output3 | X | | | | | | | | | X |
| fuzzy.output4 | | X | | | | | | X | | |
| fuzzy.output5 | | X | | | | | | | X | |
| fuzzy.output6 | | X | | | | | | | | X |
| fuzzy.output7 | | | X | | | | | X | | |
| fuzzy.output8 | | | X | | | | | | X | |
| fuzzy.output9 | | | X | | | | | | | X |
| fuzzy.output10 | | | | X | | | | X | | |
| fuzzy.output11 | | | | X | | | | | X | |
| fuzzy.output12 | | | | X | | | | | | X |
| fuzzy.output13 | | | | | X | | | X | | |
| fuzzy.output14 | | | | | X | | | | X | |
| fuzzy.output15 | | | | | X | | | | | X |
| fuzzy.output16 | | | | | | X | | X | | |
| fuzzy.output17 | | | | | | X | | | X | |
| fuzzy.output18 | | | | | | X | | | | X |
| fuzzy.output19 | | | | | | | X | X | | |
| fuzzy.output20 | | | | | | | X | | X | |
| fuzzy.output21 | | | | | | | X | | | X |

Having established Table 1, Table 2 and Table 3, the program proceeds to step 64 in which the variables fuzzy.output1-fuzzy.output21 are calculated by multiplying each nonzero value set forth in Table 3, i.e. "X" equals non-zero, with its corresponding value set forth in Table 1 and also the value set forth in Table 2. For example, assuming that the $SpO_2$ value is 0.96 and that the blood oxygen saturation level is decreasing, i.e. oldsat>sat so that fuzzy.dsn=1, fuzzy.sn is set to the value 0.6667, fuzzy.normal is set to the value of 0.333 and fuzzy.dsn is set to the value of 1. All other values are equal to 0.

Consequently, for this example fuzzy.output10 is set to 0.6667, fuzzy.output13 is set to 0.3333 and all other fuzzy.outputX values are set to zero.

The program then proceeds to step 66 in which the fuzzy rule table is implemented first by determining variables FVVLi-FMd in accordance with the following Table 4:

TABLE 4

| sat increase/decrease | fuzzy. output # | fuzzy. output # | fuzzy. output # | fuzzy. output # |
|---|---|---|---|---|
| FVVLi | 1 | 1 | | |
| FVLi | 4 | 2 | | |
| FLi | 7 | 5 | 3 | |
| FMi | 10 | 8 | 6 | |
| FSi | 13 | 11 | 9 | |
| Fzerochange | 16 | 14 | 12 | 19 |
| FSd | 18 | 17 | 15 | |
| FMd | 21 | 20 | | |

Where FVVLi-FSi represents a decreasing magnitude of change, Fzerochange represents no change and FSd-FMd represents a small to large increase.

The values FVVLi-FMd are then computed by determining the maximum value of the fuzzy.output1-21 associated with each of the variables FVVLi-FMd. For example, the variable FLi is computed by determining the maximum value of fuzzy.output7, fuzzy.output5 and fuzzy.output3. In the prior example where sat=0.96 and sat is decreasing, only fuzzy.output10 and fuzzy.output13 are non-zero. Thus from Table 4, FMi is set to 0.6667, FSi is set to 0.3333 and all other variables in FVVLi-FMd are set to zero.

The program then proceeds to step 68 in which the newDF is computed in accordance with the following equation:

$$dfiO2numerator = FVVLi*0.15 + FVLi*0.08 + FLi*0.04 + FMi*0.02 + FSi*0.005 - FSd*0.005 - FMd*0.01$$

$$dfiO2denominator = FVVLi + FVLi + FLi + FMi + FSi + \text{Fzerochange} + FSd + FMd$$

$$newDF = dfiO2numerator/dfiO2denominator$$

Step 68 also stores the value sat in the variable oldsat and calculates a temporary new $FiO_2$ "temp" in accordance with the equation temp=newDF+$FiO_2$.

The program then proceeds to steps 70–80 which, like steps 42–52 in FIG. 2, ensures that $FiO_2$ is neither greater than 1.0 nor less than 0.21 and, assuming that both conditions are met, sets $FiO_2$ to $FiO_2$+newDF. Step 80 then branches to step 72 and the program returns to step 32 (FIG. 2) in the main loop.

From the foregoing, it can be seen that the second preferred embodiment of the present invention utilizes fuzzy logic to implement control of the $FiO_2$ which varies not only as a function of the magnitude of the patient's $SpO_2$, but also as a function of the rate of change of the patient's $SpO_2$. In practice, the fuzzy logic utilized to control the calculation of $FiO_2$ is not only effective in use, but results in a much shorter weaning period than obtainable from the previously known systems.

Having described my invention, however, many modifications thereto will become apparent to those skilled in the art to which it pertains without deviation from the spirit of the invention as defined by the scope of the appended claims.

I claim:

1. A medical ventilator system comprising:
    a source of pressurized oxygen,
    a fluid conduit extending between said pressurized oxygen source and a patient,
    valve means actuatable to control an FiO2 to the patient, said valve means fluidly connected in series with said fluid conduit, means for measuring the blood oxygen saturation of the patient and providing an SpO2 signal representative thereof, and means responsive to the magnitude of the SpO2 signal and rate of change of the SpO2 signal for varying the FiO2 of the patient by variably actuating said valve means.

2. The invention as defined in claim 1 and comprising processing means utilizing fuzzy logic for variably actuating said valve means.

3. The invention as defined in claim 1 further comprising a program utilizing fuzzy logic executed by said controller for variably actuating said valve means.

4. A medical ventilator system comprising:

a source of pressurized oxygen, a fluid conduit extending between said pressurized oxygen source and a patient, valve means actuatable to control an FiO2 to the patient, said valve means fluidly connected in series with said fluid conduit, means for measuring the blood oxygen saturation of the patient and providing an SpO2 signal representative thereof, processing means using fuzzy logic for varying the FiO2 of the patient by variably actuating said valve means.

5. A medical ventilator system comprising:

a source of pressurized oxygen, a fluid conduit extending between said pressurized oxygen source and a patient, a valve actuatable to control an FiO2 to the patient, said valve fluidly connected in series with said fluid conduit, a pulse oximeter for measuring the blood oxygen saturation of the patient and providing an SpO2 signal representative thereof, and a controller responsive to the magnitude of the SpO2 signal and rate of change of the SpO2 signal for varying the FiO2 of the patient by variably actuating said valve.

* * * * *

UNITED STATES PATENT AND TRADEMARK OFFICE
CERTIFICATE OF CORRECTION

PATENT NO. : 6,761,165 B2
DATED : July 13, 2004
INVENTOR(S) : James H. Strickland, Jr.

It is certified that error appears in the above-identified patent and that said Letters Patent is hereby corrected as shown below:

Column 2,
Line 65, after "step" insert -- 30. --

Signed and Sealed this

First Day of February, 2005

JON W. DUDAS
*Director of the United States Patent and Trademark Office*